(12) United States Patent
Zeng et al.

(10) Patent No.: US 10,023,700 B2
(45) Date of Patent: Jul. 17, 2018

(54) HYDROGEL

(71) Applicant: The Governors of the University of Alberta, Edmonton (CA)

(72) Inventors: Hongbo Zeng, Edmonton (CA); Lin Li, Edmonton (CA); Bin Yan, Edmonton (CA)

(73) Assignee: The Governors of the University of Alberta

( * ) Notice: Subject to any disclaimer, the term of this patent is extended or adjusted under 35 U.S.C. 154(b) by 0 days.

(21) Appl. No.: 15/389,918

(22) Filed: Dec. 23, 2016

(65) Prior Publication Data

US 2017/0190844 A1  Jul. 6, 2017

Related U.S. Application Data

(60) Provisional application No. 62/275,498, filed on Jan. 6, 2016.

(51) Int. Cl.
*A61K 47/34* (2017.01)
*A61K 9/06* (2006.01)
*C08G 81/02* (2006.01)

(52) U.S. Cl.
CPC .............. *C08G 81/025* (2013.01); *A61K 9/06* (2013.01); *A61K 47/34* (2013.01)

(58) Field of Classification Search
CPC ..... C08G 81/025; C08J 3/075; C08J 2387/00; A61K 47/34; A61K 9/06; C08F 293/00; C08F 293/005; C08F 296/026; C08F 299/00; C08F 297/00
See application file for complete search history.

(56) References Cited

U.S. PATENT DOCUMENTS

2013/0053594 A1  2/2013  Lee et al.

OTHER PUBLICATIONS

Patil, N. et al. Polymer Chemistry vol. 6 pp. 2919-2933 (Feb. 19, 2015).*
Hasegawa, U. et al. Polymer vol. 66 pp. 1-7 (Jun. 1, 2015).*
Q. Lu, D. X. Oh, Y. Lee, Y. Jho, D. S. Hwang, H. Zeng, Angew. Chem. Int. Ed. 2013, 52, 3944.
D. S. Hwang, H. Zeng, A. Masic, M. J. Harrington, J. N. Israelachvili, J. H. Waite, J. Biol. Chem. 2010, 285, 25850.
B. K. Ahn, D. W. Lee, J. N. Israelachvili, J. H. Waite, Nature Mater. 2014, 13, 867.
Y. He, T. P. Lodge, Macromolecules 2008, 41, 167.
W. Wei, J. Yu, C. Broomell, J. N. Israelachvili, J. H. Waite, J. Am. Chem. Soc. 2012, 135, 377.
T. G. O'Lenick, N. Jin, J. W. Woodcock, B. Zhao, J. Phys. Chem. B 2011, 115, 2870.
A. Vagias, P. Košovan, K. Koynov, C. Holm, H. J. Butt, G. Fytas, Macromolecules 2014, 47, 5303.
R. Bodvik, L. Karlson, K. Edwards, J. Eriksson, E. Thormann, P. M. Claesson, Langmuir 2012, 28, 13562.
M. Salonen, M. Ellermann, F. Diederich, Angew. Chem. Int. Ed. 2011, 50, 4808.
S. Herrwerth, W. Eck, S. Reinhardt, M. Grunze, J. Am. Chem. Soc. 2003, 125, 9359.
Ostuni, R. G. Chapman, R. E. Holmlin, S. Takayama, G. M. Whitesides, Langmuir 2001, 17, 5605.
L. Mi, S. Jiang, Angew. Chem. Int. Ed. 2014, 53, 1746.
S. Rose, A. Prevoteau, P. Elzière, D. Hourdet, A. Marcellan, L. Leibler, Nature 2013, 505, 382.
J. Sedó, J. Saiz-Poseu, F. Busqué, D. Ruiz-Molina, Adv. Mater. 2013, 25, 653.
B. P. Lee, P. B. Messersmith, J. N. Israelachvili, J. H. Waite, Ann. Rev. Mater. Res. 2011, 41, 99.
E. Faure et al. Process in Polymer Science, 2013, vol. 38, 236-270.
L. Yu, J. Ding, Chem. Soc. Rev. 2008, 37, 1473.
N. A. Peppas, J. Z. Hilt, A. Khademhosseini, R. Langer, Adv. Mater. 2006, 18, 1345.
H. Park, J. S. Temenoff, Y. Tabata, A. I. Caplan, A. G. Mikos, Biomaterials 2007, 28, 3217.
D. Sivakumaran, D. Maitland, T. Hoare, Biomacromolecules 2011, 12, 4112.
A. Parisi-Amon, W. Mulyasasmita, C. Chung, S. C. Heilshorn, Adv. Healthcare Mater. 2013, 2, 428.
T. Nakai, T. Hirakura, Y. Sakurai, T. Shimoboji, M. Ishigai, K. Akiyoshi, Macromol. Biosci. 2012, 12, 475.
A. Paul, A. Hasan, H. A. Kindi, A. K. Gaharwar, V. T. Rao, M. Nikkhah, S. R. Shin, D. Krafft, M. R. Dokmeci, D. Shum-Tim, ACS nano 2014, 8, 8050.
A. L. Lee, V. W. Ng, S. Gao, J. L. Hedrick, Y. Y. Yang, Adv. Funct. Mater. 2014, 24, 1538.
B. F. Lin, K. A. Megley, N. Viswanathan, D. V. Krogstad, L. B. Drews, M. J. Kade, Y. Qian, M. V. Tirrell, J. Mater. Chem. 2012, 22, 19447.
A. López-Noriega, C. L. Hastings, B. Ozbakir, K. E. O'Donnell, F. J. O'Brien, G. Storm, W. E. Hennink, G. P. Duffy, E. Ruiz-Hernández, Adv. Healthcare Mater. 2014, 3, 854.
C. Ding, L. Zhao, F. Liu, J. Cheng, J. Gu, S. Dan, C. Liu, X. Qu, Z. Yang, Biomacromolecules 2010, 11, 1043.
Yu, H. Fan, J. Huang, J. Chen, Soft Matter 2011, 7, 7386.
Y. Zhang, Y. Sun, X. Yang, J. Hilbom, A. Heerschap, D. A. Ossipov, Macromol. Biosci. 2014, 14, 1249.
L. Tan, Y. Liu, W. Ha, L. Ding, S. Peng, S. Zhang, B. Li, Soft Matter 2012, 8, 5746.
X. Jiang, S. Jin, Q. Zhong, M. D. Dadmun, B. Zhao, Macromolecules 2009, 42, 8468.
A. Servant, V. Leon, D. Jasim, L. Methven, P. Limousin, E. V. Fernandez-Pacheco, M. Prato, K. Kostarelos, Adv. Healthcare Mater. 2014, 3,1334.
E. Brynda, N. A. Cepalova, M. Štol, J. Biomed. Mater. Res. 1984, 18, 685.

(Continued)

*Primary Examiner* — Irina S Zemel
*Assistant Examiner* — Jeffrey S Lenihan
(74) *Attorney, Agent, or Firm* — Anthony R. Lambert

(57) ABSTRACT

A novel mussel-inspired injectable hydrogel with self-healing and anti-biofouling capabilities is developed, possessing great potential as drug delivery carrier. The hydrogel can heal autonomously from repeated structural damage and also effectively prevent nonspecific cell attachment and biofilm formation.

6 Claims, 8 Drawing Sheets

(56) References Cited

OTHER PUBLICATIONS

B. Wehrle-Haller, Cuff. Opin. Cell. Biol. 2012, 24, 569.
M. Black, A. Trent, Y. Kostenko, J. S. Lee, C. Olive, M. Tirrell, Adv. Mater. 2012, 24, 3845.
T. Kakuta, Y. Takashima, M. Nakahata, M. Otsubo, H. Yamaguchi, A. Harada, Adv. Mater. 2013, 25, 2849.
A. Phadke, C. Zhang, B. Arman, C. C. Hsu, R. A. Mashelkar, A. K. Lele, M. J. Tauber, G. Arya, S. Varghese, Proc. Natl. Acad. Sci. U.S.A. 2012, 109, 4383.
Y. Amamoto, J. Kamada, H. Otsuka, A. Takahara, K. Matyjaszewski, Angew. Chem. Int. Ed. 2011, 123, 1698.
Y. Amamoto, H. Otsuka, A. Takahara, K. Matyjaszewski, Adv. Mater. 2012, 24, 3975.
P. Cordier, F. Tournilhac, C. Soulie-Ziakovic, L. Leibler, Nature 2008, 451, 977.
A. Faghihnejad, K. E. Feldman, J. Yu, M. V. Tirrell, J. N. Israelachvili, C. J. Hawker, E. J. Kramer, H. Zeng, Adv. Funct. Mater. 2014, 24, 2322.
D. Liu, D. Wang, M. Wang, Y. Zheng, K. Koynov, G. K. Auernhammer, H.J. Butt, T. Ikeda, Macromolecules 2013, 46, 4617.
Y. Zhao, F. Sakai, L. Su, Y. Liu, K. Wei, G. Chen, M. Jiang, Adv. Mater. 2013, 25, 5215.
Y. Liu, K. Ai, L. Lu, Chem. Rev. 2014, 114, 5057.
B. Yang, N. Ayyadurai, H. Yun, Y. S. Choi, B. H. Hwang, J. Huang, Q. Lu, H. Zeng, H. J. Cha, Angew. Chem. Int. Ed. 2014, 53,13360.
N. Holten-Andersen, M. J. Harrington, H. Birkedal, B. P. Lee, P. B. Messersmith, K. Y. C. Lee, J. H. Waite, Proc. Natl. Acad. Sci. U.S.A. 2011, 108, 2651.
M. Krogsgaard, M. A. Behrens, J. S. Pedersen, H. Birkedal, Biomacromolecules 2013, 14, 297.
L. He, D. E. Fullenkamp, J. G. Rivera, P. B. Messersmith, Chem. Commun. 2011, 47, 7497.
M. Vatankhah-Varnoosfaderani, S. Hashmi, A. GhavamiNejad, F. J. Stadler, Polymer Chemistry 2014, 5, 512.
B. J. Kim, D. X. Oh, S. Kim, J. H. Seo, D. S. Hwang, A. Masic, D. K. Han, H. J. Cha, Biomacromolecules 2014, 15, 1579.
H. Zeng, D. S. Hwang, J. N. Israelachvili, J. H. Waite, Proc. Natl. Acad. Sci. U.S.A. 2010, 107, 12850.
Q. Lu, D. S. Hwang, Y. Liu, H. Zeng, Biomaterials 2012, 33, 1903.

\* cited by examiner

FIG. 5A
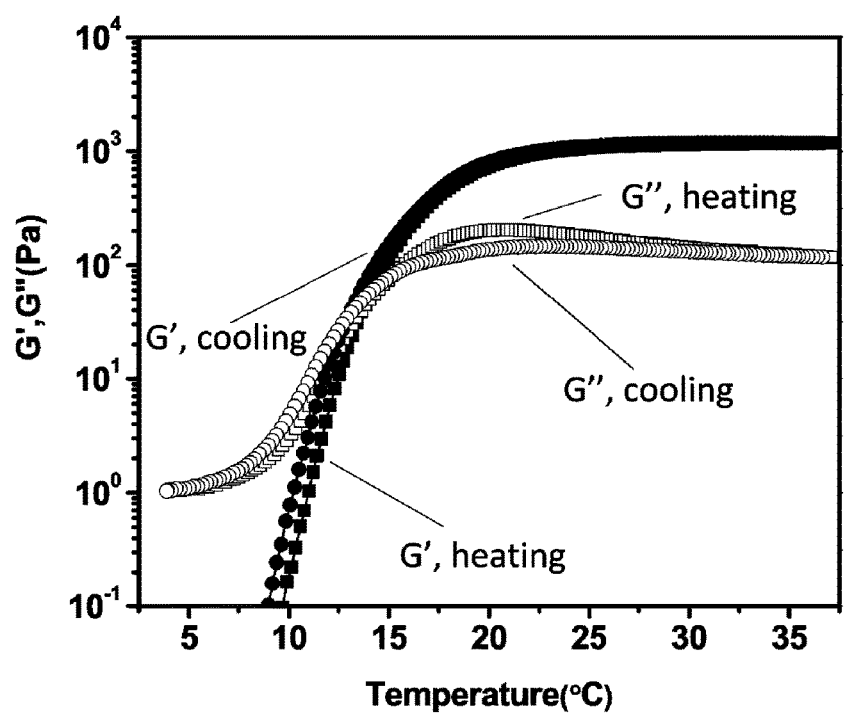
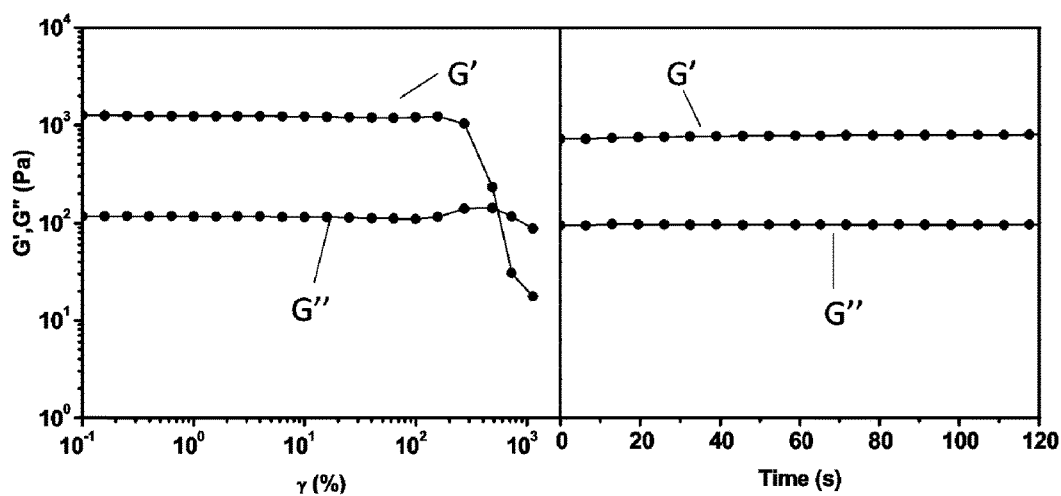
FIG. 5B

HYDROGEL

TECHNICAL FIELD

Hydrogels.

BACKGROUND

Injectable hydrogels are emerging as promising materials for biomedical applications like drug delivery because of their biocompatibility, ease of administration and minimal invasion due to their high resemblance with natural extracellular matrices. Bioactive molecules like drugs, proteins, DNA and antibodies can be easily mixed with precursor solutions and loaded at target site via an in-situ gelation right after the injection. The release of these bioactive molecules can be performed in a sustainable or burst way on demand in response to external stimuli such as change in temperature or pH, introduction of redox or biomolecules, and exposure to light or electric field. Encapsulated in hydrogel matrix, the loaded molecules can be maximally protected from unnecessary enzymatic degradation or hydrolyzation to retain their bioactivity, before triggered for releasing to target cells or tissues by external stimuli to fulfil their therapeutical potential. However, proteins or microorganisms could easily adhere to implanted hydrogels and form biofouling films, not only blocking the circulation of loaded biomolecules but also triggering an immune response or inflammation.

A common means to address this challenging issue is to confer the developed hydrogels antifouling or antimicrobial properties to minimize accumulation of biofouling films on their surfaces. Nonetheless, the outcome of this approach is quite limited because implanted hydrogels after injection suffer from constant external mechanical force, which could lead to certain deformation or damage of the hydrogels. Once disruption takes place in vivo, body fluids will intrude and simultaneously introduce nutrients and microorganisms to build up detrimental biofoulings, consequently shortening the lifespan of the hydrogel materials used and inducing further inflammatory responses. In this circumstance, a hydrogel possessing autonomous healing capability after inflicted damage will be of great significance to extend its application and lifespan, because the integrity of the broken hydrogel fragments after injection could be recovered at the target site under physiological conditions, preventing a burst release of the loaded biomolecules and enhancing delivery efficiency. The healable networks are usually constructed through interactions such as dynamic covalent bonding, noncovalent linkages, host-guest interactions and hydrogen bonding. Recently marine mussel has inspired various applications in diverse fields, among which the preparation of self-healing hydrogels inspired by the self-repair of mussel threads is of great significance. Marine mussels secrete foot proteins which after a curing process can form byssus consisting of proteinaceous thread and adhesive plaque to adhere to various substrates underwater. The self-repair of mussel byssal threads is mainly attributed to the reversible metal-catechol coordination between metals like $Fe^{3+}$ and catechol groups from an amino acid called 3,4-Dihydroxyphenyl-L-alanine (DOPA), and other interactions like cation-$\pi$ interaction can also play a role. Very recently, self-repair was also demonstrated in metal-free water of synthetic polyacrylate and polymethacrylate surface-functionalized with catechols through catechol-mediated interfacial hydrogen bonds.

SUMMARY

In an embodiment, there is a disclosed a polymer comprising at least one block A and one block B, where A is a thermo-responsive copolymer comprising at least one monomer having a lower critical solution temperature and at least one self-healing monomer and B is a hydrophilic polymer block. Block A may be formed of a random copolymer. The random copolymer may comprise DN where D is dopamine acrylamide and N is NIPAM. The self-healing property may be provided by catechol and/or aromatic groups.

BRIEF DESCRIPTION OF THE FIGURES

Embodiments will now be described with reference to the figures, in which like reference characters denote like elements, by way of example, and in which:

FIG. 5A shows temperature-responsive storage (G') and loss (G") modulus changes of a 10 wt % BNOBN hydrogel.

FIG. 5B shows strain sweep measurements of a 10 wt % BNOBN hydrogel at 37° C. (left) and time-dependent recovery from the strain failure (right). The modulus recovery was around 57%.

DETAILED DESCRIPTION

Figure 1A:
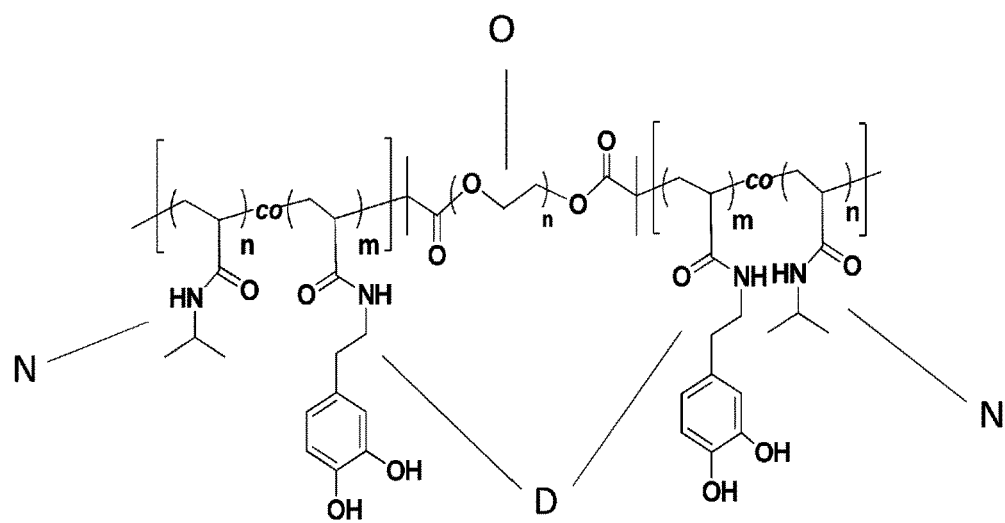
FIG. 1A shows the chemical structure of an exemplary ABA triblock copolymer DNODN.

Disclosed is a new type of injectable hydrogel based on self-assembly of a copolymer with rapid self-healing properties through mussel-inspired catechol-mediated hydrogen bonding interactions and aromatic interactions and with anti-biofouling capability. In an embodiment, the polymer comprises at least one block A and one block B, where A is a thermo-responsive copolymer comprising at least one lower critical solution temperature monomer "a" and at least one self-healing monomer "b" (such as mussel-inspired DOPA monomer) and B is a hydrophilic polymer block. A thermo-responsive polymer is characterized by having certain properties, such as polarity, solubility, or hydrophobicity, altered by changes in temperature; in an embodiment, the thermo-responsive copolymer in aqueous solution changes from hydrophilic to hydrophobic when the temperature increases above the temperature of phase separation. Self-healing is the intrinsic capability for the materials that enables them to automatously recover its original functions via re-formation of bonds or interactions without external stimulus. The level of self-healing should be at least a modulus recovery of 70%, though it is preferred to be 100% as achieved with DNODN. Hydrophilic means that the polymer is water-soluble (and has strong attraction to water).

The block copolymer could be in the form A-B, A-B-A, B-A-B A-B-C, or similar polymer structures, with varying polymer architectures like star-shaped, grafted or hyperbranched copolymers. The responsive copolymer block A could be in the random or statistical form of a and b. The polymer block C could be thermoresponsive copolymer block which is the same or similar as the block A, or different copolymer block comprising hydrophobic monomers. The A block may be DN as disclosed herein or an equivalent in some embodiments. For example, a may be poly(N-isopropylacrylamide) (PNIPAM) and b may be N-3,4-dihydroxyphenethyl acrylamine. Polymer block B is hydrophilic, which may comprise poly(ethylene oxide), zwitterionic polymers such as phosphobetaine, sulfobetaine and phospholipid polymers having a phosphorylcholine group, or may comprise other hydrophilic polymers like poly(2-methyl-2-oxazoline), polysaccharides and poly(oligo(ethylene glycol) methyl ether methacrylate). Hydrophobic monomers added to the block A may include homopolymer or copolymers with polymerization degree between 30 to 50 of the less-soluble monomers include acrylonitrile; methacrylonitrile; alkyl methacrylate and alkyl acrylate such as methyl methacrylate and methyl acrylate, ethyl methacrylate and ethyl acrylate, butyl methacrylate and butyl acrylate, ethylhexyl methacrylate and ethylhexyl acrylate; vinyl acetate; alkyl methacrylamide and alkyl acrylamide such as methyl methacrylamide and methyl acrylamide, ethyl methacrylamide and ethyl acrylamide, butyl methacrylamide and butyl acrylamide, ethylhexyl methacrylamide and ethylhexyl acrylamide; styrene and its derivatives; and N-vinylimidazole and its derivatives, or combinations thereof.

In an embodiment, mussel-inspired catechol-functionalized poly(N-isopropylacrylamide) (PNIPAM) copolymerized with N-3,4-dihydroxyphenethyl acrylamine and poly(ethylene oxide) (PEO) were selected as the thermo-sensitive A block and hydrophilic B block of the copolymer, respectively.

The triblock copolymer poly[(N-isopropylacrylamide)-co-(N-3,4-dihydroxyphenethyl acrylamine)]-b-poly(ethylene oxide)-b-poly[(N-isopropylacrylamide)-co-(N-3,4-dihydroxyphenethyl acrylamine)] (DNODN, FIG. 1A) was synthesized by a combination of reversible additional fragment transfer (RAFT) polymerization and a sequent replacement between an active ester and dopamine as described below. The hydrogel prepared through self-assembly of this DNODN triblock copolymer exhibited a fast thermo-responsive sol-to-gel transition and could heal autonomously from repeated damage. In addition, the DNODN hydrogel exhibited an excellent antifouling performance against nonspecific cell attachment due to the presence of a major component PEO possessing strong antifouling property. It is also interesting to note that the catechol-functionalized PNIPAM A block provides a hydrophobic microenvironment which effectively retards the oxidation of catechol groups, a tricky and smart strategy adopted by marine mussels.

The structure of an embodiment DNODN is shown in FIG. 1A, where O is a hydrophilic polymer block, PEO in this embodiment, N represents NIPAM and D represents dopamine acrylamide. The DN block in DNODN is a random copolymer so includes all variants NDODN, DNODN or DNOND. For purposes of this disclosure, the variants are described as DNODN for consistency.

There are two different functional polymer blocks in DNODN triblock copolymer: one is the hydrophilic PEO block (O) and the other the thermos-responsive one (DN). PEO block endows the resultant hydrogel with antifouling property and guarantees the hydrogel could hold a large amount of water. In principle, the EO unit of PEO block could be tuned from 45 to 900 or even higher. But preferably, it is chosen to be 225 to 450, which could not only satisfy the requirements for antifouling property and holding suitable water in hydrogels but also simplify the synthesis and purification.

As for the thermo-responsive block DN, the ratio of these two components of N for NIPAM and D for dopamine acrylamide determines the final applicable temperature for the DNODN hydrogel. If only these two components, N and D, are involved, the obtained hydrogel could have a sol-gel transition temperature ranging from 5° C. to 35° C. when D/N ratio in DN block changes from ½ to 0. For example, with l=455 for PEO units, m=56 D units and n=227 N units, the obtained hydrogel has sol-gel transition temperature of 16° C.

If a higher sol-gel transition temperature above 35° C. is desired for the DNODN hydrogel, a water-soluble or hydrophilic component, W, may be incorporated into DN block. The component of W may comprise neutral water-soluble monomer like acrylamide, oligo (ethylene glycol) methyl ether acrylate, N-Hydroxyethyl acrylamide, N,N-Dimethylacrylamide, 2-Hydroxypropyl methacrylamide, and N-[Tris(hydroxymethyl)methyl]acrylamide; or ionisable or zwitterionic monomers such as acrylic acid, 2-(Dimethylamino)ethyl methacrylate, [2-(Methacryloyloxy)ethyl]dimethyl-(3-sulfopropyl)ammonium hydroxide, 2-Methacryloyloxyethyl phosphorylcholine, [2-(Methacryloyloxy)ethyl]trimethyl-ammonium chloride, 3-Sulfopropyl methacrylate, (3-Acrylamidopropyl)trimethylammonium chloride, 2-Acrylamido-2-methyl-1-propanesulfonic acid. With the ratio of W among DN block between 5 mol % to 20 mol %, it is possible to tune the sol-gel transition temperature from 35° C. to 70° C. For example, with l=455 for PEO units, m=56 for D units and n=227 for N units, x=70 for W units of (3-Acrylamidopropyl)trimethylammonium chloride, the obtained hydrogel would have a sol-gel transition of 60° C.

In an embodiment that provides thermo-responsiveness and injectability of the resulting hydrogel, the A block is a thermo-responsive polymer DN with a suitable incorporation of D units for example from 5 mol % to 30 mol % providing self-healing property. Basically, DN polymer block is a random copolymer of D and N units so that there is no constraint for the ordering and repeats. For ordering of blocks in DNODN triblock copolymer, the hydrophilic part PEO may be in the middle block or at an end, though preferably two thermoresponsive DN blocks are at both sides of PEO.

The N part is the thermoresponsive component in the DNODN, which basically can be replaced by all kinds of thermo-sensitive polymers such as poly(N,N-diethylacrylamide), poly(N-vinylcaprolactam), poly[2-(dimethylamino)

ethyl methacrylate], poly(ethylene glycol) methacrylate polymers (PEGMA) having a side-PEG chain of 2-10 ethylene oxide units (EO)<10, since these have similar properties The polymer block O or poly(ethylene oxide) provides antifouling property, and may comprise zwitterionic polymers such as phosphobetaine, sulfobetaine and phospholipid polymers having a phosphorylcholine group, or may comprise hydrophilic polymer like poly(2-methyl-2-oxazoline), polysaccharides and poly(oligo (ethylene glycol) methyl ether methacrylate), since these have similar properties. In terms of catechol groups which endows hydrogel with self-healing property, they can be catechol derivatives like 2-nitrodopamine and 2-chlorodopamine, or multi-hydrogen bonding groups such as 2-ureido-4[1H]pyrimidinone, since these have similar properties. Based on the results presented here for DNODN, these other combinations forming A and B blocks should work the same. In another example, based on these results, the combination DNOBN should also work, where BN is described below.

Figure 1B:
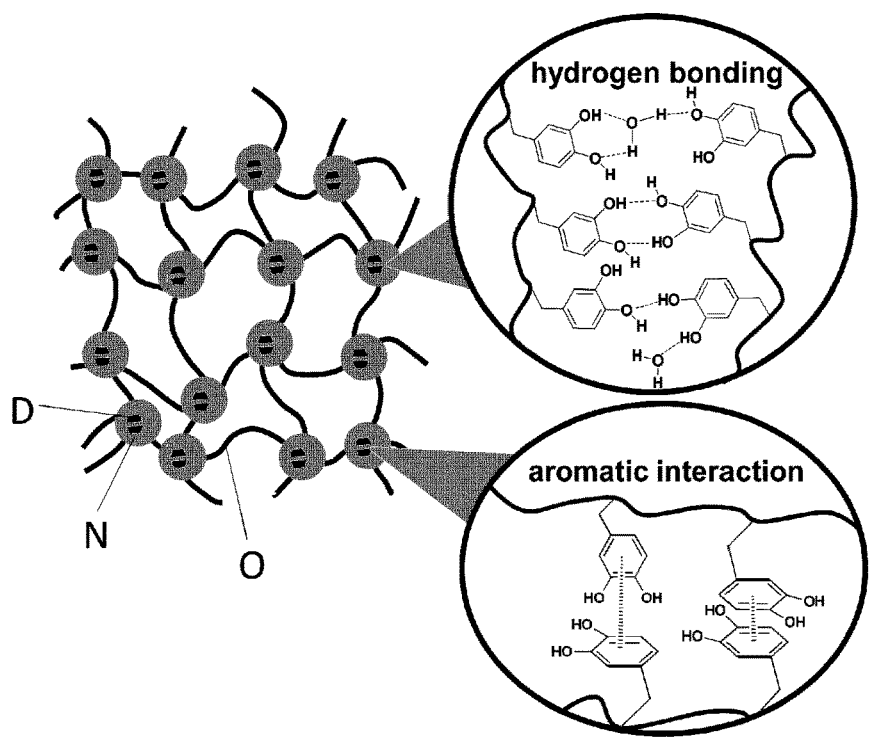
FIG. 1B shows a schematic of a proposed structure of an exemplary DNODN hydrogel.
Figure 2A:
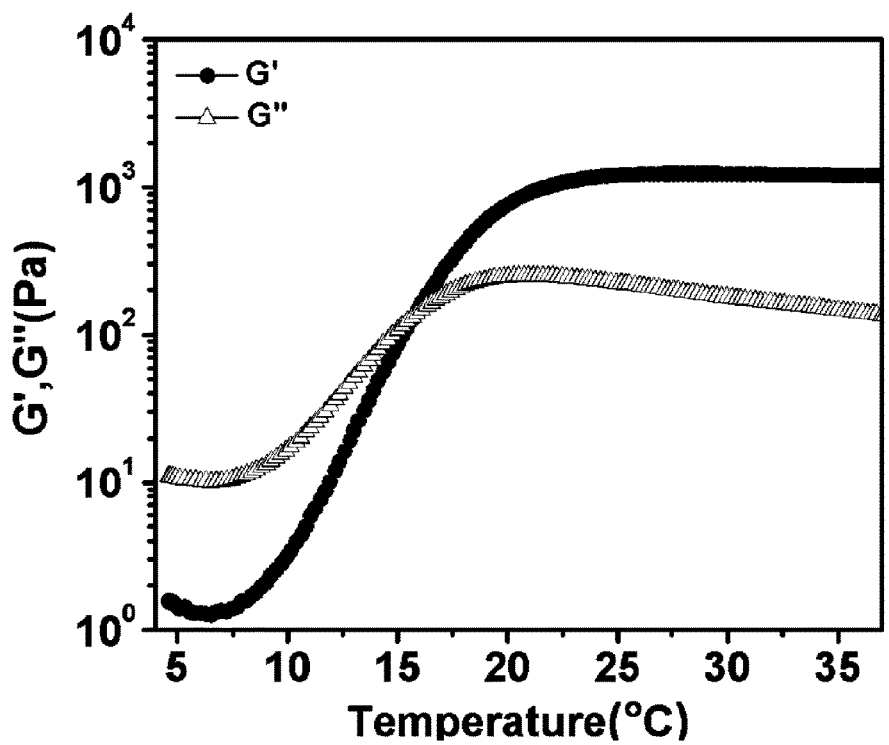
FIG. 2A shows the temperature-responsive storage (G') and loss (G") modulus changes of a 10 wt % DNODN hydrogel.
Figure 2B:
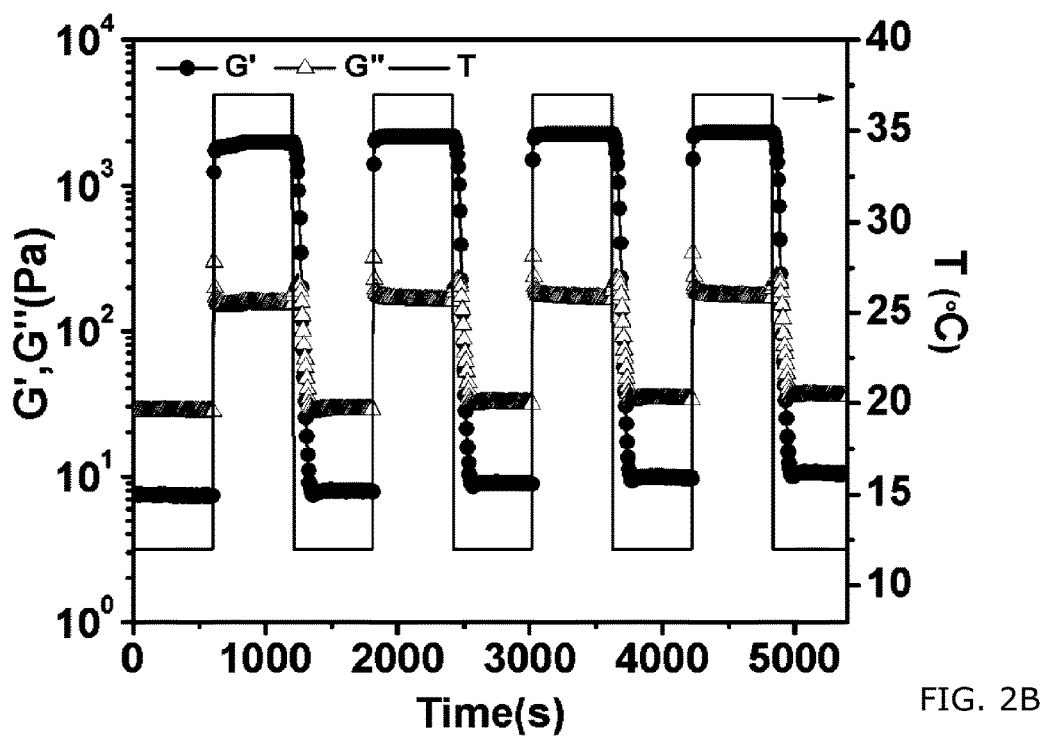
FIG. 2B shows the modulus changes of a 10 wt % DNODN hydrogel with thermal cycles of heating (37° C.) and cooling (12° C.) for four rounds.
Figure 2C:
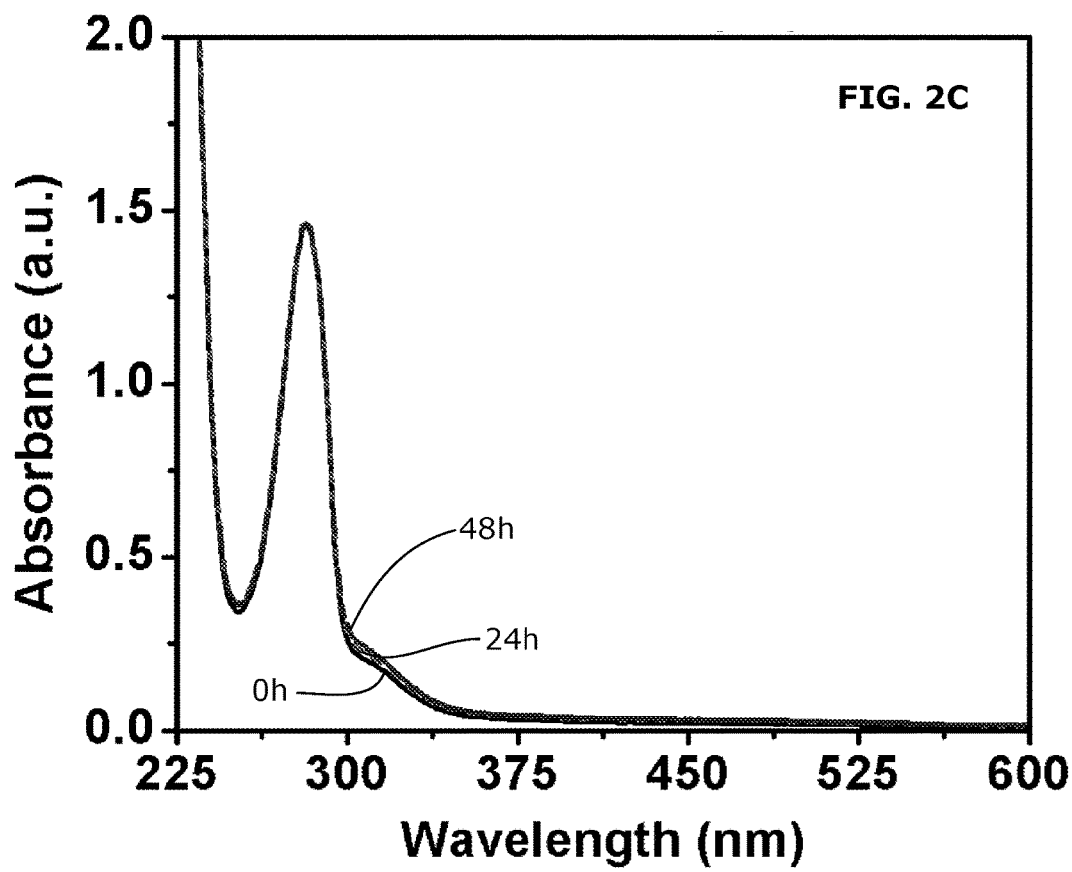
FIG. 2C shows the UV/Vis spectra of a DNODN solution (1 mg/ml in DI water) tracked within 48 h at room temperature under air atmosphere.

There will now be disclosed detailed characterization and method of manufacture of DNODN, a specific example of an AB hydrogel. In the embodiment shown of DNODN, since A blocks are thermosensitive and B blocks are permanently water-soluble, increasing solution temperature would lead to the formation of a three-dimensional network with the dehydrated A blocks associating into micellar cores and the central B blocks forming bridges (FIG. 1B). A sample of 10 wt % DNODN is a free-flow viscous liquid at a lower temperature (i.e. 4° C.) but becomes a free-standing gel when warmed to room temperature. The thermo-sensitivity of the DNODN hydrogel was first characterized with a temperature ramp test using a rheometer, in which storage modulus G' and loss modulus G" were recorded from 4° C. to 37° C. at a heating rate of 1° C./min, as shown in FIG. 2A. The angular frequency ($\omega$) and strain ($\gamma$) were held constant at 10 rad/s and 5%, respectively. At lower temperatures, G" was greater than G', signifying a liquid-like property. While with the heating process, G' increased significantly faster than G" and became much larger than G" at higher temperature, indicating a gel-like property. The crossover between G' and G" at 16° C. was identified as the sol-gel transition temperature. To rule out the possibility that thermal-induced gelation was due to cathechols' coupling reactions after oxidation, dynamic temperature sweep measurements between 12° C. and 37° C. were conducted (FIG. 2B), with angular frequency ($\omega$) and strain ($\gamma$) held constant at 10 rad/s and 5%, respectively. It was observed that the sol-gel-sol transitions were totally reversible during the cyclic tests, indicating that the hydrogel is not constructed through irreversible quinone cross-linking but through hydrophobic interactions arisen from PNIPAM at high temperature. UV-Vis absorption spectra of DNODN solution (1 mg/ml) at room temperature (22° C.) under air atmosphere were tracked within 48 h and shown in FIG. 2C. Characteristic absorption peak of catechol groups at 280 nm was clearly observed and remained unchanged, demonstrating the catechol groups remained unoxidized, which was consistent with the fact that the DNODN solution (1 mg/ml) retained clear within the experimental period. Since the lower critical solution temperature (LCST) of DNODN was measured as 15° C. by dynamic light scattering, the polymer chains aggregated into micelles with hydrodynamic diameter ~43 nm at room temperature, indicating an encapsulation of catechol groups in the micellar cores. For comparison, a dopamine hydrochloride solution (0.23 mg/ml) with same concentration of catechol groups as that of DNODN solution was prepared and it was found that its catechol groups were easily oxidized within 5 h with visible color change. The DNODN hydrogel's insusceptibility to oxidation is mainly attributed to the local hydrophobic microenvironment provided by the catechol functionalized poly(N-isopropyl acrylamide) A blocks at temperature above the sol-gel transition temperature. Such a protection mechanism is consistent with previous study that DOPA in mussel foot protein 3 (Mfp3) is less prone to oxidation because the high proportion of hydrophobic amino acid residues in Mfp3 sequence provides DOPA with a microenvironment that retards oxidation by shielding the amino acids from external oxidants. The excellent thermo-reversibility together with the low modulus (<10 Pa) at low temperature endow the novel DNODN hydrogel injectable properties: when the 4° C.-preserved polymer solution was injected into a water bath at 37° C. using a 23G×¾" syringe, it immediately turned into stable hydrogel.

Figure 3A:
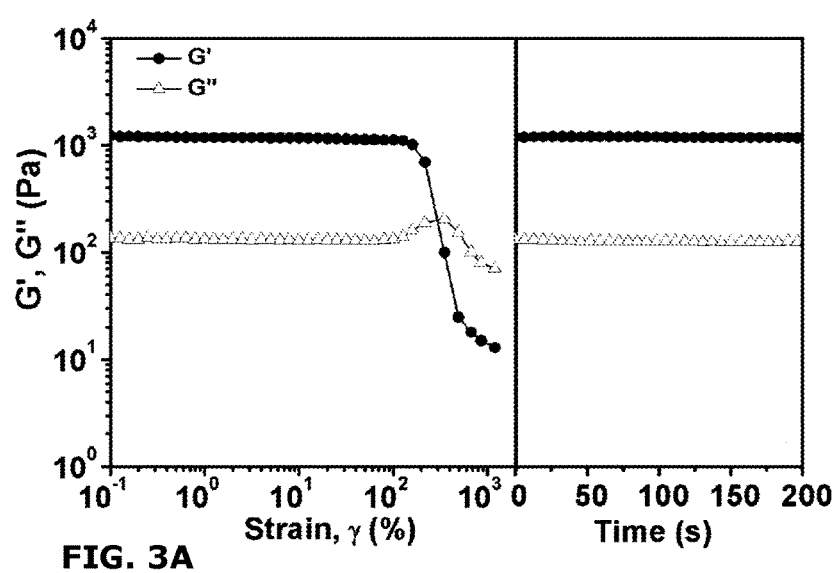
FIG. 3A shows strain sweep measurements of a 10 wt % DNODN hydrogel at 37° C. (storage modulus G' and loss modulus G" as a function of strain $\gamma$) (left) and an immediate recovery from the 1000% strain deformation (right).
Figure 3B:
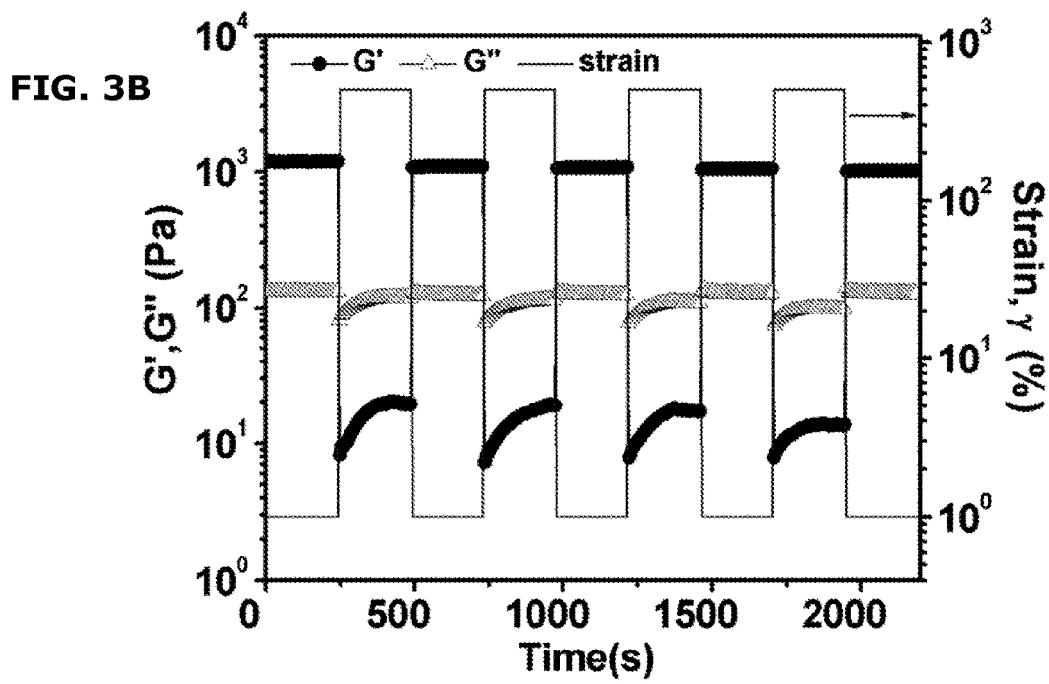
FIG. 3B shows dynamic strain amplitude cyclic test ($\gamma$=1% or 500%) of 10 wt % DNODN hydrogel at 37° C. showing self-healing behaviour.
Figure 3C:
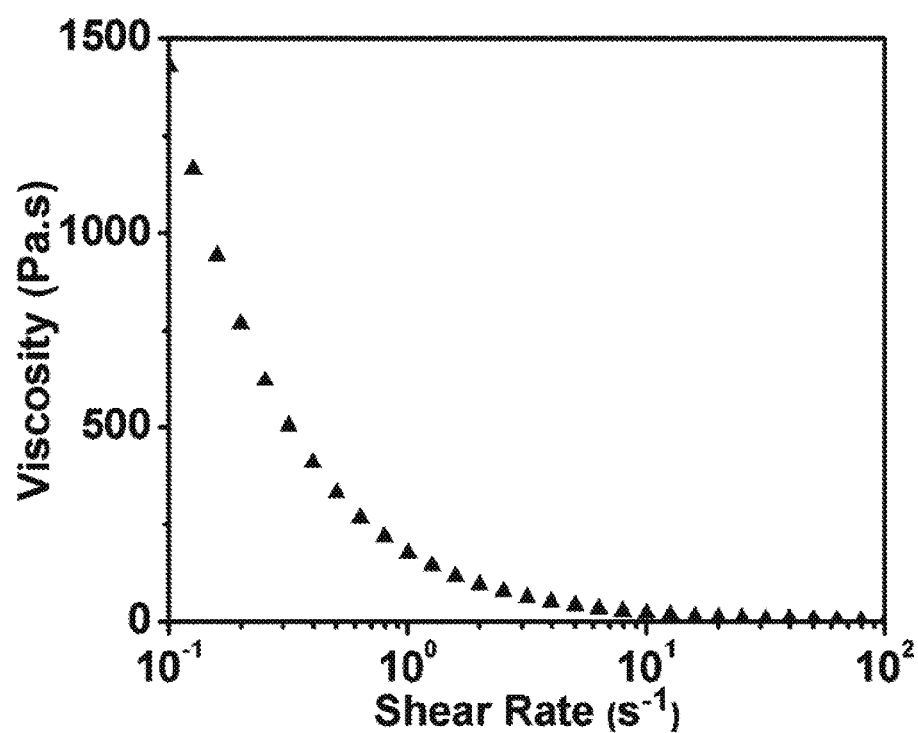
FIG. 3C shows viscosity measurement on a 10 wt % DNODN hydrogel at 37° C.

For an injectable hydrogel as a qualified drug delivery depot, it is essential that the hydrogel could rapidly self-heal and restore to its original gel state after inflicted damage. Therefore, strain sweep measurements were conducted on the DNODN hydrogel (10 wt %) to test its responsive behaviour upon external strains. FIG. 3A shows that G' and G" remained constant until the strain reached 100%, suggesting the formed free-standing hydrogel could withstand relatively large deformations. (The angular frequency and temperature were held constant at 10 rad/s and 37° C., respectively.) However when the applied strain $\gamma$ was further increased, a dramatic drop was observed for both G' and G" values and a crossover occurred at around strain $\gamma=400\%$, indicating that beyond this critical strain point severe dislocation of polymer chains occurred and disrupted the hydrogel network which turned into a sol state. It was found that the mechanical properties of the hydrogel could be fully recovered if a 1% strain test was immediately followed after severe strain deformation ($\gamma=1000\%$) in FIG. 3A. Meanwhile, repeated dynamic strain step tests ($\gamma=1\%$ or 500%) were applied on the DNODN (10 wt %) hydrogel. As presented in FIG. 3B, when subjected to a 500% strain, G' immediately dropped from ~1200 Pa to around 20 Pa. (The angular frequency and temperature were held constant at 10 rad/s and 37° C., respectively.) Upon the strain returned to 1%, both G' and G" were able to recover the initial values without any loss. This recovery process could be completed almost instantly (within several seconds). This recovery behaviour was totally reversible and reproducible during the cyclic tests. This self-healing property of the novel DNODN hydrogel was observed visually in further experiments where two hydrogel fragments could adhere to each other instantly when brought into contact and automatically heal into one integral piece. The healed hydrogel could withstand vigorous shaking and maintain its integrity. Viscosity measurement on a 10 wt % DNODN hydrogel at 37° C. and 5% strain was conducted and a reduction in viscosity with increasing shear rate was observed (FIG. 3C). This shearing thinning behaviour resulting from the disruption of physical cross-links would provide broken segments with higher mobility within the hydrogel matrix, which may be an explanation to this self-healing property.

Figure 1C:
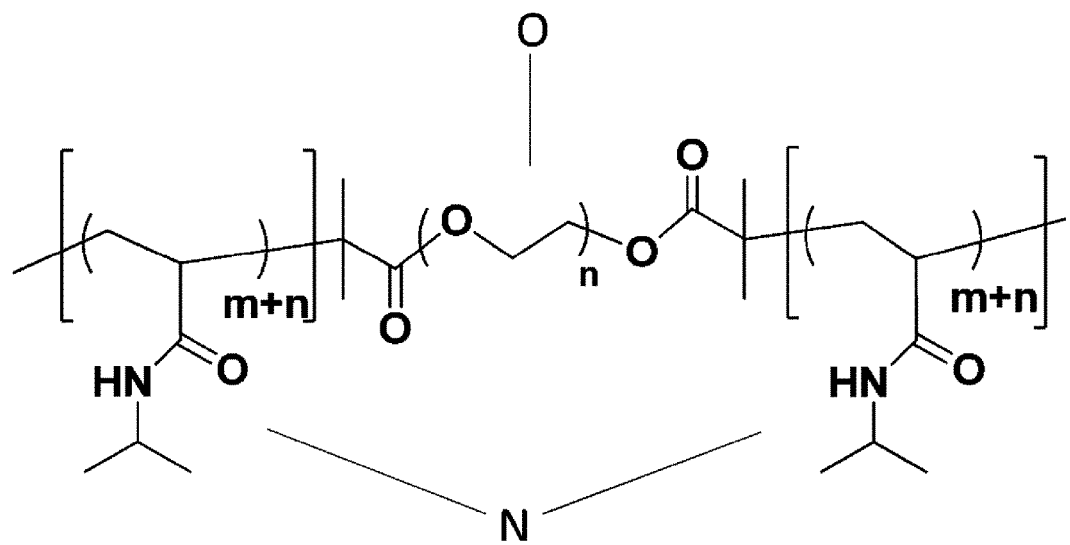
FIG. 1C shows the chemical structure of tri-block copolymer NON for comparison with DNODN.
Figure 4A:
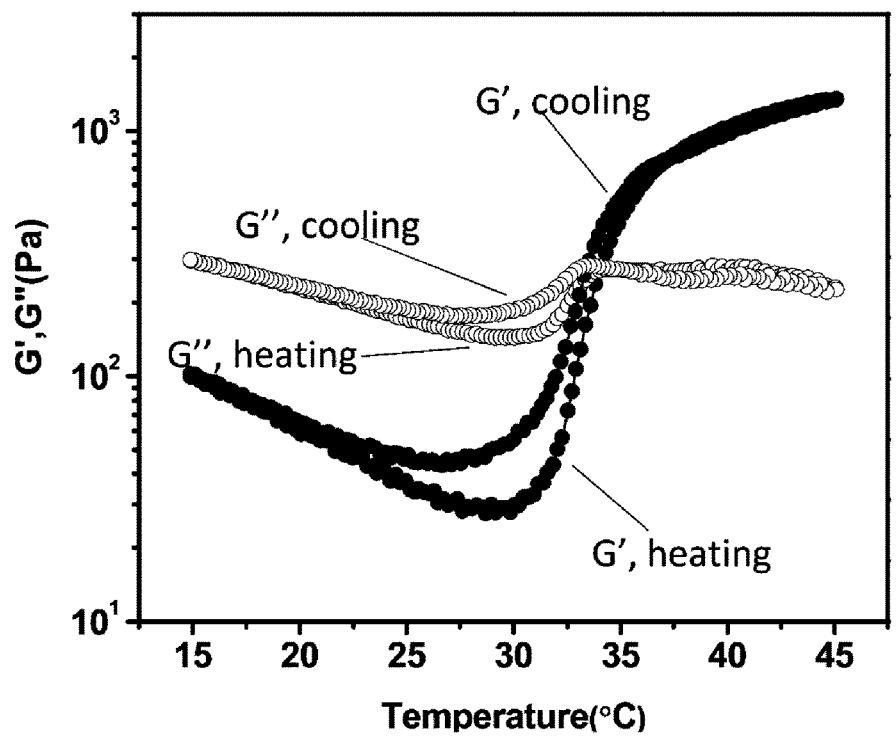
FIG. 4A shows temperature-responsive storage (G') and loss (G") modulus changes of a 10 wt % NON hydrogel.
Figure 4B:
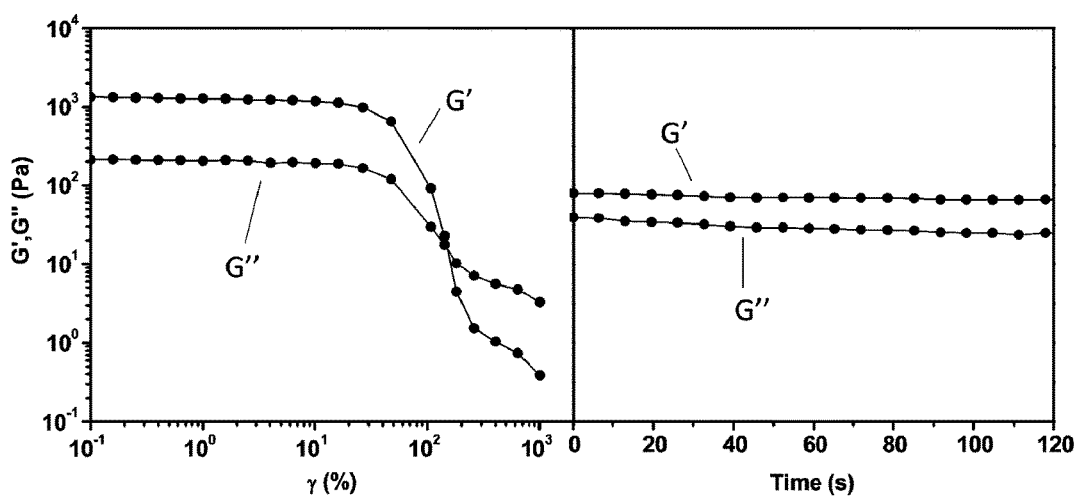
FIG. 4B shows strain sweep measurements of a 10 wt % NON hydrogel at 45° C. (left) and time-dependent recovery from the strain failure (right). The modulus recovery was ~25%.

To better understand the self-healing mechanism of the DNODN hydrogel, a fully oxidized hydrogel was prepared by adding $NaIO_4$ to freshly-prepared DNODN hydrogel. The treated hydrogel sample lost its thermo-reversibility and self-healing property, and turned into a permanent hydrogel due to the irreversible quinone cross-linking. Meanwhile, an ABA triblock copolymer without functionalization of catechol groups (NON, FIG. 1C) with PNIPAM as A block and PEO as the middle B block was synthesized. A 10 wt % NON hydrogel showed good thermo-reversibility (FIG. 4A, with angular frequency ($\omega$) and strain ($\gamma$) held constant at 10 rad/s and 5%, respectively) but its modulus recovery from severe strain deformation ($\gamma$=1000%) was only 25% (FIG. 4B, with angular frequency of 10 rad/s and temperature of 45° C., and 1% strain in the right panel). It is evident from the above results that the unoxidized catechol groups play an important role in achieving the remarkable self-healing performance through hydrogen bonding (FIG. 1B). Such a proposed mechanism agrees with the recent results by Israelachvili, Waite and co-workers on interfacial self-healing of synthetic polyacrylate and polymethacrylate surface-functionalized with catechols.

Figure 1D:
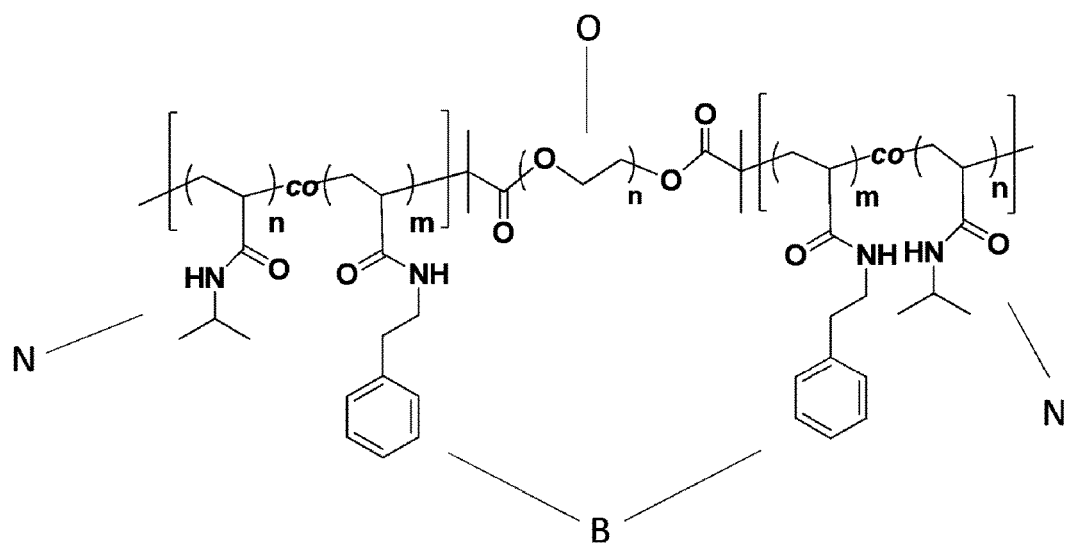
FIG. 1D shows the chemical structure of tri-block copolymer BNOBN for comparison with DNODN.

However, it should be noted that whether hydrogen bonding between interfacial catechol moieties plays the sole role in the self-healing of the DNODN hydrogel still remains unclear. To fully elucidate the mechanism, another ABA tri-block copolymer (BNOBN, FIG. 1D) with A block from random copolymerization of phenylethylacrylamide and NIPAM and B block PEO was also synthesized. A 10 wt % BNOBN hydrogel showed good thermo-reversibility (FIG. 5A, with angular frequency and strain held constant at 10 rad/s and 5%, respectively) and the modulus recovery from severe strain deformation ($\gamma$=1000%) could reach 57% (FIG. 5B, with angular frequency of 10 rad/s and temperature of 37° C., and 1% strain in the right panel), indicating that aromatic interactions including quadrupolar interactions (edge-to-face) and $\pi$-$\pi$ stacking interactions could also contribute to the self-healing mechanism (FIG. 1B). A freshly-prepared DNODN gel piece and a periodate-oxidized one were brought together for healing. It was found that the two gel pieces could adhere to each other but could be separated relatively easily right at the contact interface, indicating a reduced healing performance as compared with that between two freshly-prepared DNODN hydrogel pieces. Since the strength of hydrogen bonding between asymmetric catechol-quinone surfaces is comparable to or stronger than that between symmetric catechol-catechol surfaces, the reduced healing performance should be attributed to the weaker aromatic interactions (i.e. most likely the weakened quadrupolar interactions between quinones and catechols) and restrained chain mobility due to oxidized cross-linking, further indicating that aromatic interactions including quadrupolar and $\pi$-$\pi$ stacking interactions play considerable roles in achieving the self-healing property of DNODN hydrogel. To sum up, it is evident from the above results that (i) the shear-thinning behaviour of the DNODN hydrogel enhances the mobility of polymer chains and catechol groups to interact with each other during self-healing, and (ii) both hydrogen bonding and aromatic interactions including quadrupolar and $\pi$-$\pi$ stacking interactions between interfacial catechol groups play important roles in achieving this remarkable self-healing performance.

The novel DNODN hydrogel also shows exceptional antifouling performance against cell attachment, studied by seeding human intestinal Caco-2 cells directly onto the hydrogel-coated microwell dishes followed by fluorescence imaging. Fluorescence microscopy was used to detect the presence of Caco-2 cells on uncoated and DNODN hydrogel coated microwell dishes after exposure to the Caco-2 cells for 48 h. Caco-2 cells attached to the glass bottom of the microwell dishes readily, forming a dense cell layer. In contrast, DNODN hydrogel coated microwell dishes showed exceptional resistance to cell attachment, which could be attributed to the presence of a major component PEO and the inherent structure of the whole hydrogel. The tri-block copolymer DNODN exhibited good biocompatibility within the experimental concentrations (up to 5 mg/ml).

Materials:

All chemicals for polymer synthesis were purchased from Sigma Aldrich and were used as received. Thermo-sensitive monomers, T, such as N-isopropylacrylate (NIPAM), N,N-diethylacrylamide (DEA), N-vinylcaprolactam, 2-(dimethylamino)ethyl methacrylate (DMAEMA), poly(ethylene glycol) methacrylate having a side-PEG chain of 2-10 ethylene oxide units (EO)<10, water-soluble monomers, W, like acrylamide, oligo (ethylene glycol) methyl ether acrylate, N-Hydroxyethyl acrylamide, N,N-Dimethylacrylamide, 2-Hydroxypropyl methacrylamide, and N-Tris(hydroxymethyl)methyl]acrylamide; or ionisable or zwtterionic monomers such as acrylic acid, 2-(Dimethylamino)ethyl methacrylate, [2-(Methacryloyloxy)ethyl]dimethyl-(3-sulfopropyl)ammonium hydroxide, 2-Methacryloyloxyethyl phosphorylcholine, [2-(Methacryloyloxy)ethyl]trimethylammonium chloride, 3-Sulfopropyl methacrylate, (3-Acrylamidopropyl)trimethylammonium chloride, 2-Acrylamido-2-methyl-1-propanesulfonic acid are from Aldrich. Poly(ethylene oxide) with different molecular weight like 5000, 10000 and 20000 Daltons were purified by precipitating in hexane three times and dried under vacuum overnight. Perfluorophenyl acrylate (PFPA) was synthesized according to a reported procedure. Alexa Fluor dyes and 4,6-diamidino-2-phenylindole (DAPI) were from Life Technologies (burlington, ON, Canada). Human intestinal Caco-2 cell line, the Caco-2 cell basel medium, the Caco-2 cell growth kit (low serum), Trypsin-EDTA and Trypsin neutralizing solution were purchased from the American Type Culture Collection (ATCC, Manassas, Va., USA).

Polymer Synthesis:

ABA triblock copolymers can be synthesized by using different living polymerization methods such as atom transfer radical polymerization (ATRP) and reversible Addition-Fragmentation chain Transfer (RAFT) polymerization. RAFT polymerization is demonstrated as an example and the tri-block copolymer comprising mussel-inspired catechol-functionalized thermo-responsive polymer and poly(ethylene oxide) (PEO) was synthesized by a combination of RAFT polymerization and sequent replacement between an active ester and dopamine. First, RAFT-PEO$_{455}$-RAFT was used as a macro-RAFT initiator to generate two thermo-responsive polymer blocks by reacting with one of the thermo-responsive monomers T, one of the water-soluble monomers W, and pentafluorophenyl acrylate at the desired molar ratios. Through this, a precursor ABA triblock copolymer was obtained that can be replaced with dopamine or its derivatives to be mussel-inspired thermo-responsive ABA triblock copolymers.

Macro-RAFT agent RAFT-PEO$_{455}$-RAFT was synthesized by attaching the chain transfer agent (S)-1-dodecyl-(S')-($\alpha$,$\alpha$'-dimethyl-$\alpha$"-acetic acid) trithiocarbonate to ends of PEO$_{455}$ precursor following a reported procedure.

In terms of the procedures mentioned in the preceding paragraphs, they are two commonly adopted methods to prepare functional monomers pentaflourophenyl acrylate (PFPA) and PEO based macro-RAFT initiator for synthesis of DNODN triblock copolymers. A typical example for PFPA synthesis is shown as follows: Pentaflourophenol (5.4 g, 29.3 mmol), 3.5 ml 2.6-lutidine (30.0 mmol) and dichloromethane (50 ml) were added into a 500 ml round-bottom flask. After cooling the whole mixture to 0° C., a solution of acryloyl chloride (2.6 ml, 31.9 mmol) in 20 mL dichloromethane was added dropwise and the whole mixture stirred for 3 h at 0° C. and kept stirring at room temperature overnight. After filtration of the solution to remove the precipitated 2.6-lutidine hydrochloride, the filtrate was washed twice with 30 ml water and dried over $MgSO_4$. The solvent was removed and the targeted product was obtained as a colorless liquid (5.2 g, 75%) by distillation of the remaining liquid distilled under reduced pressure at 0.05 mbar. A small amount of di-tert-butyl-p-cresol was added to avoid polymerization during the distillation. To obtain PEO based macro-RAFT initiator, (S)-1-dodecyl-(S')-($\alpha,\alpha'$-dimethyl-$\alpha''$-acetic acid) (1.0 g, $2.7 \times 10^{-3}$ mol) was mixed with excess oxalyl chloride (1.5 g, 0.012 mol) in dry dichloromethane (4 mL) under argon atmosphere and stirred at room temperature for 4 hr. Excess reagents were then removed under vacuum, and the residue was redissolved in dry dichloromethane (50 mL) followed by the addition of PEG (5.5 g, $2.7 \times 10^{-4}$ mol). The reaction proceeded overnight at room temperature. After that, the product were precipitated four times in diethyl ether (500 mL) and dried in a vacuum oven.

In a typical synthesis experiment, RAFT-$PEO_{455}$-RAFT agent (0.518 g, 0.025 mmol), N-isopropylacrylamide (1.130 g, 10 mmol), pentafluorophenyl acrylate (0.238 g, 1 mmol) and azobisisobutyronitrile (0.002 g, 0.0125 mmol) were dissolved in 3 ml dioxane. After purging $N_2$ for 15 min, the whole system was stirred at 78° C. for 2 h. The polymerization was quenched by adding 5 mL THF into the above mixture and the resulted solution was added dropwise into a great amount of ethyl ether to precipitate the polymer out. Afterwards the filtered polymer was redissolved in THF and precipitated twice into an excess amount of ethyl ether. The polymer was dried under vacuum overnight and 1.681 g of the polymer was obtained. The composition of the resulting polymer was characterized by $^1$H NMR and was determined as Poly[($NIPAM_{227}$-co-$PFPA_{56}$)]-b-$PEO_{455}$-Poly[($NIPAM_{227}$-co-$PFPA_{56}$)]. $^1$H NMR ($CDCl_3$, 400 MHz): $\delta_H$ (ppm)=4.0 (s, O=C—NH—CH—$(CH_3)_2$), 3.64 (m, —$CH_2CH_2O$—), 2.49 (br, —$CH_2$—CH(CONH)—), 1.68-1.4 (br, —$CH_2$—CH(CONH)—, $CH_2$—CHCOO), 1.1 (s, O=C—NH—CH—$(CH_3)_2$). PNIPAM-b-PEO-b-PNIPAM (NON) was synthesized following the same procedure shown above except that no PFPA was added during polymerization. The obtained polymer was characterized as $PNIPAM_{300}$-b-$PEO_{455}$-b-$PNIPAM_{300}$. $^1$H NMR ($CDCl_3$, 400 MHz): $\delta_H$ (ppm)=4.0 (s, O=C—NH—CH—$(CH_3)_2$), 3.64 (m, —$CH_2CH_2O$—), 2.49 (br, —$CH_2$—CH(CONH)—), 1.68 (br, —$CH_2$—CH(CONH)—), 1.1 (s, O=C—NH—CH—$(CH_3)_2$).

Poly[(NIPAM-co-N-3,4-dihydroxyphenethylamine acrylamide)]-b-PEO-b-poly[(NIPAM-co-N-3,4-dihydroxyphenethylamine acrylamide)] (DNODN) and poly[(NIPAM-co-phenethyl-amineacrylamide)]-b-PEO-b-poly[(NIPAM-co-phenethylamine acrylamide)] (BNOBN) were synthesized by substituting pentafluorophenyl group with the corresponding amine groups such as N-3,4-dihydroxyphenethylamine and phenethylamine. A typical example of DNODN was given as follows: Poly[($NIPAM_{227}$-co-$PFPA_{56}$)]-b-$PEO_{455}$-Poly[($NIPAM_{227}$-co-$PFPA_{56}$)] (1.681 g) and dopamine hydrochloride (0.380 g, 2 mmol) were mixed in 20 mL dichloromethane. After 20 min Argon purging, triethylamine (0.202 g, 2 mmol) was added and the whole mixture was stirred overnight at 50° C. The resulting polymer was precipitated with ethyl ether twice and obtained as a white solid. The catechol functionalized polymer DNODN-1 was obtained as Poly[($NIPAM_{227}$-co-(N-3,4-dihydroxyphenethyl acrylamine$_{56}$)]-b-$PEO_{455}$-b-Poly[($NIPAM_{227}$-co-(N-3,4-dihydroxyphenethyl acrylamine$_{56}$)]. $^1$H NMR ($CDCl_3$, 400 MHz): $\delta_H$ (ppm)=6.8–6.5 (m, $CH_2C_6H_3(OH)_2$), 4.0 (s, O=C—NH—CH—$(CH_3)_2$), 3.64 (m, —$CH_2CH_2O$—), 3.4 (q, $CH_2$—NHC(O)), 2.6 (m, $CH_2$—$C_6H_3(OH)_2$) 2.49 (br, —$CH_2$—CH(CONH)—), 1.68 (br, —$CH_2$—CH (CONH)—), 1.1 (s, O=C—NH—CH—$(CH_3)_2$). DNODN-1 has a gel-sol transition temperature of 16° C. To prepare DNODN-2 with a gel-sol transition temperature of 37° C., the similar procedure as DNODN-1 was adopted with exception that 5 mol % of water-soluble monomer, Tris(hydroxymethyl)methyl]acrylamide, was added together with NIPAM and PFPA. DNODN with different gel-sol transition temperature were obtained by replacing NIPAM with other thermo-responsive monomers such as DEA, DMAEMA or poly(ethylene glycol) methacrylate having a side-PEG chain of 2-10 ethylene oxide units (EO)<10 and incorporating a suitable ratio of water soluble monomers.

As a control to investigate the effect of catechol on the self-healing properties of the obtained hydrogels, BNOBN was synthesized using phenethylamine in the above procedure and obtained as poly[($NIPAM_{227}$)-co-(phenylethylacrylamide$_{56}$)]-b-$PEO_{455}$-b-poly[($NIPAM_{227}$)-co-(phenylethylacrylamide$_{56}$)]. $^1$H NMR ($CDCl_3$, 400 MHz): $\delta_H$ (ppm)=6.8–6.5 (m, $CH_2C_6H_5$), 4.0 (s, O=C—NH—CH—$(CH_3)_2$), 3.64 (m, —$CH_2CH_2O$—), 3.4 (q, $CH_2$—NHC(O)), 2.6 (m, $CH_2$—$C_6H_3(OH)_2$) 2.49 (br, —$CH_2$—CH(CONH)—), 1.68 (br, —$CH_2$—CH(CONH)—), 1.1 (s, O=C—NH—CH—$(CH_3)_2$).

In other embodiments, the hydrophilic B block of the copolymer may comprise substances other than PEO. In another example, ABA triblock copolymer hydrogels with an antifouling B block comprising poly(2-Methacryloyloxyethyl phosphorylcholine) PMPC were synthesized as follows. Synthesis of difunctional macro-RAFT based on poly (2-Methacryloyloxyethyl phosphorylcholine) PMPC: MPC (2.95 g, 0.01 mol), RAFT agent, 1,6-bis(4-cyano-4-(ethylsulfanyl-thiocarbonylsulfanyl)pentanoic acid)hexane diamide (0.0243 mg, 0.04 mmol), initiator, AIBN (1.6 mg, 0.01 mmol), and DMSO (5 mL) was purged with $N_2$ for 15 min. The resulting yellow solution was heated at 70° C. for 3 hr and then dialyzed against water for 2 days (MWCO=3500 g/mol) to remove solvent and residual monomer. The polymer was lyophilized to obtain 2 g of a yellow powder and by $^1$H NMR, it was determined as $PMPC_{200}$.

PMPC (1.18 g, 0.02 mmol), NIPAM (0.57 g, 5 mmol), dopamine acrylate (DOA) (0.104 g, 0.5 mmol) and azobisisobutyronitrile (AIBN) (0.002 g, 0.0125 mmol) were dissolved in 3 ml DMSO. After purging $N_2$ for 15 min, the whole system was stirred at 78° C. for 2 h. The product was obtained by dialysis against acidic water (pH=3) for 2 days followed by lyophilisation. The composition of the resulting polymer was characterized by 1H NMR and was determined as Poly[($NIPAM_{180}$-co-$DOA_{23}$)]-b-$PMPC_{200}$-b-Poly[($NIPAM_{180}$-co-$DOA_{23}$)]. The obtained polymer has the similar thermal and self-healing properties as DNODN and its hydrogel has a gel-sol transition temperature of 25° C. By using the similar procedure for preparation of DNODN, this series of ABA block copolymers of with different gel-sol temperature are also accessible by introducing different molar ratio of water-soluble monomers during RAFT polymerization. In addition, instead of phospholipid polymers having a phosphorylcholine group as its middle antifouling block, it may comprise zwitterionic polymers such as phosphobetaine, sulfobetaine and may comprise hydrophilic polymer like poly(2-methyl-2-oxazoline), polysaccharides and poly(oligo (ethylene glycol) methyl ether methacrylate).

Hydrogel Preparation:

All hydrogels were prepared by dissolving corresponding polymers to DI water with a concentration of 10 wt %. The polymer solutions were stored in 4° C. before following characterizations.

Dynamic Light Scattering Study:

The hydrodynamic diameters of the copolymer at different temperatures between 0-40° C. were measured using a zetasizer (Malvern, Zetasizer Nano ZSP). The temperature where a sudden increase in particle size occurred was determined as the lower critical solution temperature (LCST).

UV-Vis Spectrometry:

UV-Vis absorption spectra of a DNODN solution (1 mg/ml) at room temperature under air atmosphere were tracked for 48 h using a UV-Vis spectrometer (Thermo Fisher Scientific, EVO300).

Oscillatory Rheology:

A Rheometer (TA instruments, AR-G2) was used to study the rheological properties of all prepared hydrogels with a 20-mm parallel-plate configuration. For 10 wt % DNODN hydrogel, the plate was set at 0° C. before the polymer solution was dropped. Temperature ramp experiments were conducted within the range of 4-37° C. to study its thermo-sensitive sol-gel transition behavior, with a heating rate of 1° C./min. A temperature cyclic step tests between 12° C. and 37° C. was also carried out, with angular frequency ($\omega$) and strain ($\gamma$) held constant at 10 rad/s and 5%, respectively. The amplitude oscillation was conducted at 37° C. and 10 rad/s, the strain was raised from 0.1% to 1000% to achieve a strain failure, followed by a time-dependent modulus observation at 1% strain. Finally a strain step cycled between 1% and 500% was performed at 37° C. and 10 rad/s.

For the 10 wt % NON hydrogel, temperature ramp experiments were conducted within the range of 15-45° C. (due to a higher LCST transition temperature than the other two hydrogels) with a heating and cooling rate of 1° C./min. The amplitude oscillation was conducted at 45° C. and 10 rad/s, the strain was raised from 0.1% to 1000% to achieve a strain failure, followed by a time-dependent modulus observation at 1% strain. For 10 wt % BNOBN hydrogel, temperature ramp experiments were conducted within the range of 4-37° C. with a heating and cooling rate of 1° C./min. The amplitude oscillation was conducted at 37° C. and 10 rad/s, the strain was raised from 0.1% to 1000% to achieve a strain failure, followed by a time-dependent modulus observation at 1% strain.

The transition temperature of a 10 wt % NON hydrogel was measured as 34° C., which was much higher than that of a 10 wt % DNODN hydrogel (16° C.). This could be interpreted that the introduction of catechol groups increased the hydrophobicity of the copolymer, thus decreased the transition temperature. The transition temperature of a 10 wt % BNOBN hydrogel was measured as 14° C., which was even lower than that of a 10 wt % DNODN hydrogel. This could also be easily understood as phenethyl groups were more hydrophobic than the catechol groups. The strain failure and recovery tests of these hydrogels showed that the 10 wt % NON hydrogel exhibited little self-healing property as the modulus recovery after strain failure was only 25%. However, the modulus recovery of 10 wt % BNOBN reached 57%, indicating that aromatic interactions also contribute to the reconstruction of hydrogel networks after inflicted damage.

Antifouling Assay:

A thin layer of DNODN hydrogel was formed on the glass bottom of the microwell dishes (P35G-1.5-14-C, MatTek Corp., USA). Normal glass bottom microwell dishes without hydrogel were used as control test. Caco-2 cells were seeded onto the dishes and cultured for 2 days until a confluent cell layer was developed. The cells were then washed with PBS and fixed with 4% paraformaldehyde (w/v in PBS). Then Alexa Fluor 488 and DAPI were used to stain the cell membrane and the nuclei respectively. The hydrogel-coated microwell dish and the control were observed under a confocal laser scanning microscopy (CLSM 510 Meta, Carl Zeiss, Jena, Germany) equipped with a ZEN 2009LE software.

Figure 6:
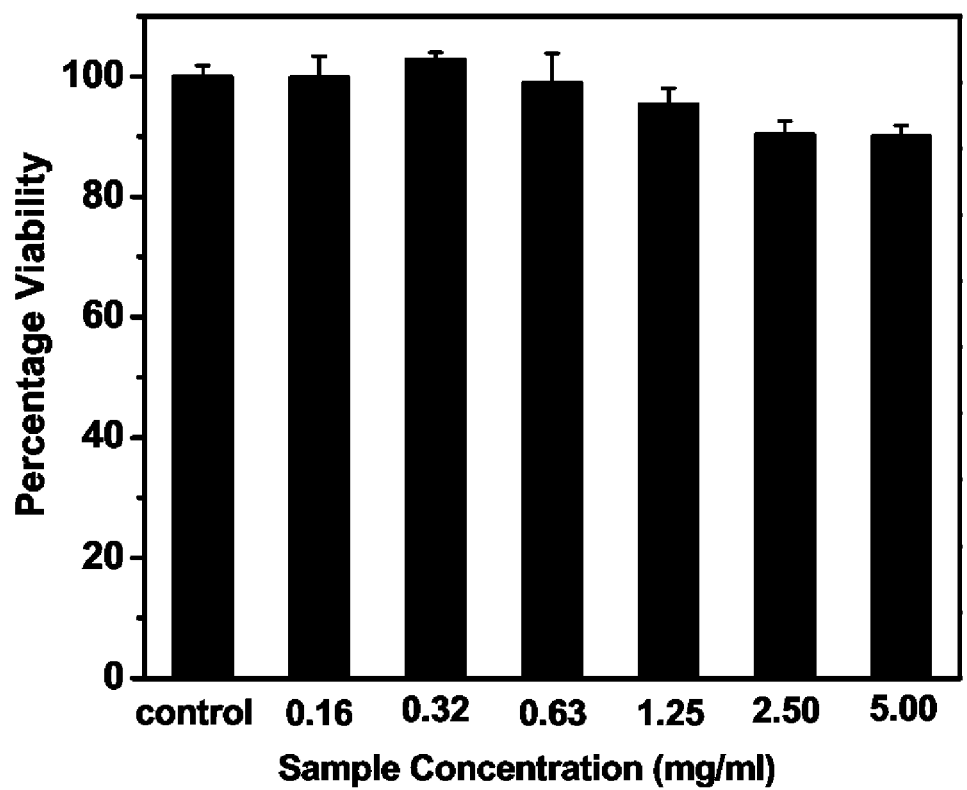
FIG. 6 shows cell viability measurements of DNODN polymer with different concentrations by MTT assay after 24 h of incubation. Data were presented as means±standard deviations (n=5).

Cytotoxicity Assay:

The cytotoxicity of the DNODN polymer was evaluated by MTT assay. Caco-2 cells were seeded into 96-well plates at a density of $8\times10^3$ cells/well in 100 µL medium. These cells were allowed to grow for 24 h before the assay. Then different volumes of diluted DNODN polymer solutions were added to each well to reach a final concentration of 5.00, 2.50, 1.25, 0.63, 0.32 and 0.16 mg/ml, respectively. DNODN polymer and cells were incubated together for 24 h before 10 µL MTT solvent (5 mg/ml in PBS) was added to each well. After incubation for 4 h, medium was removed from each well and 100 µL of DMSO was added to dissolve the purple MTT formazan crystals. The intensity of the color was read at 570 nm using a microplate reader (SpectraMax, Molecular Devices, USA) and the viability was defined as the percentage of living cells with respect to that in the control test. The cell viability measurements are shown in FIG. 6.

In summary, we have developed a novel injectable thermo-sensitive self-healing hydrogel, for example DNODN, with anti-biofouling property, based on self-assembly of a mussel-inspired triblock copolymer in metal-free aqueous environment. The thermo-sensitive property and shearing thinning behavior of the hydrogel allow it injectable in vivo at body temperature, and the anti-biofouling properties can effectively inhibit the formation of biofilms. The self-mending hydrogel, for example DNODN, can withstand high strain and repeated deformation and quickly recover its mechanical properties and structure through the catechol-mediated reconstruction of hydrogen bonding and aromatic interactions, thus reducing the inflammation risk in bioengineering applications because of the body fluids' intrusion to damaged gel matrix in injection and burst release of loaded bio-active molecules. Compared with the mussel-inspired self-healing materials constructed through catechol-metal coordination which may cause certain cytotoxicity when brought in vivo, the novel hydrogel materials developed exhibits great potential in various bioengineering applications (e.g. drug delivery), endowed with its inherent metal-free self-healing nature, thermo-sensitivity, injectability, and anti-biofouling properties.

Due to its high water content and tissue-like mechanic property, the hydrogel can be possibly used as cell culturing media. In addition, by changing the temperature above lower critical solution temperature (LCST), it is possible to tune the mechanical strength of the hydrogel, i.e., the storage moduli increases with increment of temperature, which is a common means adopted in cellular science to trigger differentiation of stem cells and allows for harvesting different tissues in the future.

Because of existence of hydrophobic and hydrophilic environments in the hydrogel, the hydrogel is an excellent drug delivery vehicle to sustainably release two kinds of model drugs (hydrophobic and hydrophilic) in targeted locations.

It is well known that catechol groups have a specific affinity to boronic ester which is highly dependent on pH and a lot of antimicrobial and anticancer drugs are based on boronic ester. As a result, the hydrogel could be easily modified into a smart platform for specific drug release, in which a burst release mode of desired drugs into tumored tissues is able to be conferred by acid-weakening catechol-boronic ester bonding. This strategy could significantly increase the drug selectivity to the tumors and reduce their toxicity to normal cells, which will dramatically enhance the viability of the patients.

Immaterial modifications may be made to the embodiments described here without departing from what is covered by the claims.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A polymer comprising at least one block A and one block B, where A is a thermo-responsive copolymer comprising at least one monomer having a lower critical solution temperature and at least one self-healing monomer and B is a hydrophilic polymer block, in which A is formed of a random copolymer and the random copolymer comprises DN where D is dopamine acrylamide and N is NIPAM.

2. The polymer of claim 1 having the structure:

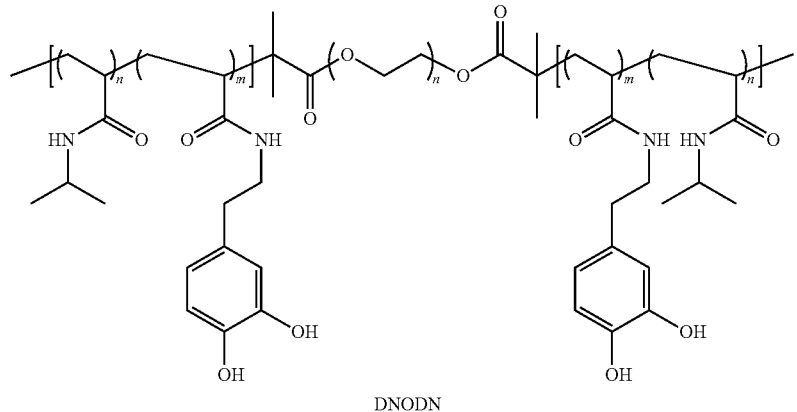

DNODN

3. A polymer comprising at least one block A and one block B, where A is a thermo-responsive copolymer comprising at least one monomer having a lower critical solution temperature and at least one self-healing monomer and B is a hydrophilic polymer block, in which the self-healing monomer is provided with a self-healing property at least in part by catechol groups.

4. The polymer of claim 3 in which A is formed of a random copolymer.

5. The polymer of claim 3 in which the self-healing monomer is provided with a self-healing property at least in part by aromatic groups.

6. The polymer of claim 5 in which A is formed of a random copolymer.

* * * * *